United States Patent [19]

Kreylos et al.

[11] Patent Number: 4,627,136
[45] Date of Patent: Dec. 9, 1986

[54] METHOD OF MANUFACTURING DENTURES

[75] Inventors: Hans-Albert Kreylos, Langen; Manfred P. Zeiser, Schwieberdingen, both of Fed. Rep. of Germany

[73] Assignee: Guenter Ruebeling, Bremerhaven, Fed. Rep. of Germany

[21] Appl. No.: 374,604

[22] Filed: Apr. 30, 1982

[30] Foreign Application Priority Data

May 13, 1981 [DE] Fed. Rep. of Germany ....... 3118890
Apr. 5, 1982 [EP] European Pat. Off. ........ 82102899.0

[51] Int. Cl.[4] ............................................. B23P 13/02
[52] U.S. Cl. .................. 29/160.6; 219/69 M; 433/218; 433/223
[58] Field of Search ...................... 29/160.6; 219/69 E, 219/69 M; 433/218, 219, 223, 191–193

[56] References Cited

U.S. PATENT DOCUMENTS

| 2,194,790 | 3/1940 | Gluck | 433/223 |
| 3,685,115 | 8/1972 | Scott | 29/160.6 |
| 4,100,388 | 7/1978 | Meyer | 219/69 E |
| 4,363,627 | 12/1982 | Windeler | 219/69 M |

FOREIGN PATENT DOCUMENTS

757180  9/1956  United Kingdom ............... 433/219

*Primary Examiner*—Howard N. Goldberg
*Assistant Examiner*—P. W. Echols
*Attorney, Agent, or Firm*—Michael J. Striker

[57] ABSTRACT

A method of manufacturing of artificial teeth, in which a primary and a secondary part of the artificial tooth or the denture are preformed, then grooves for receiving a connecting element are produced in both parts by sparking erosion, and the connecting element is inserted thereafter into the secondary and primary parts. In order to precisely align the grooves in both parts of the denture those grooves may be formed by sparking erosion in one working step.

14 Claims, 18 Drawing Figures

FIG. 5
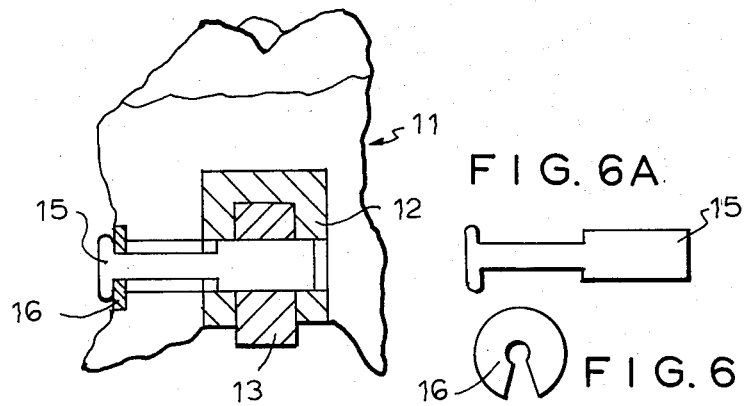
FIG. 6A
FIG. 6
FIG. 4
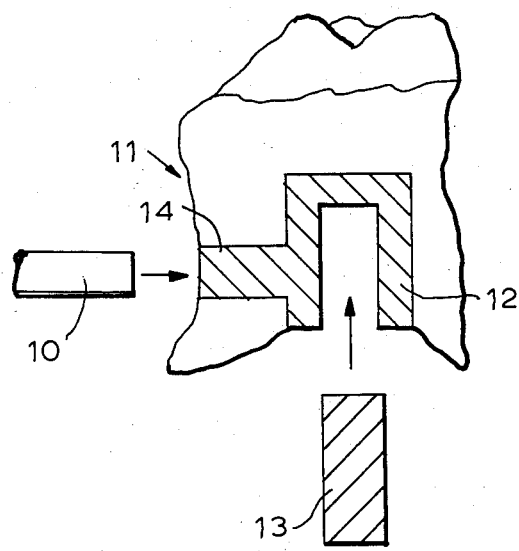

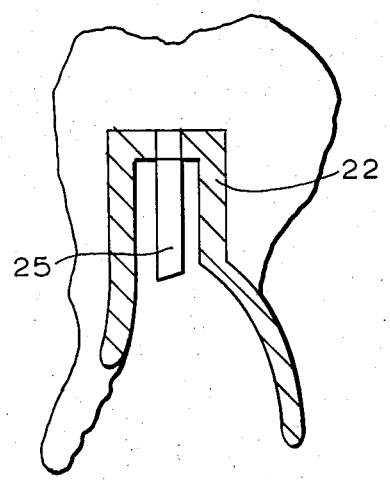
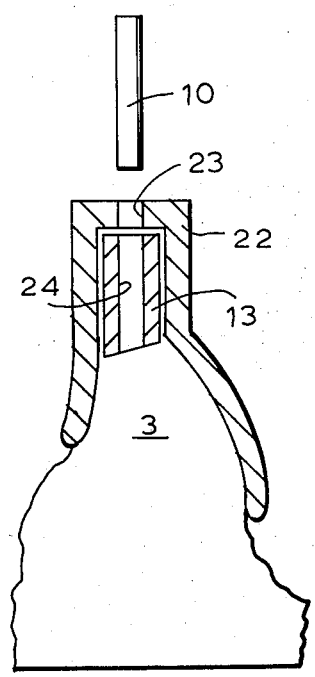
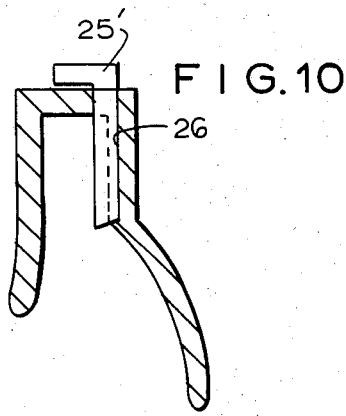
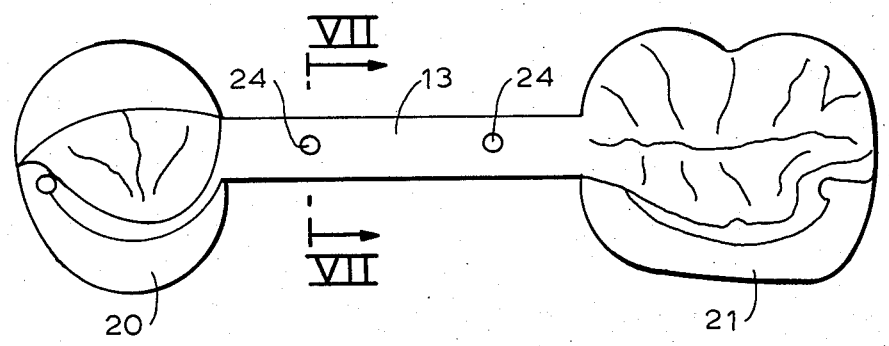

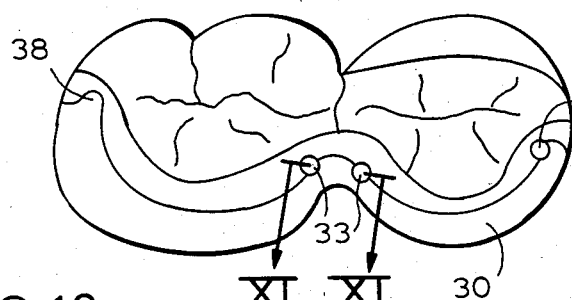
FIG. 11
FIG. 12
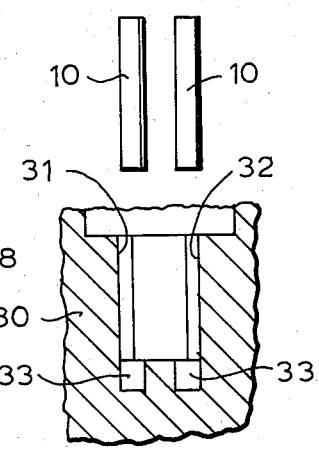
FIG. 13
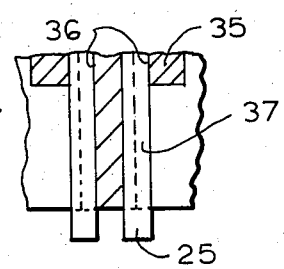
FIG. 14
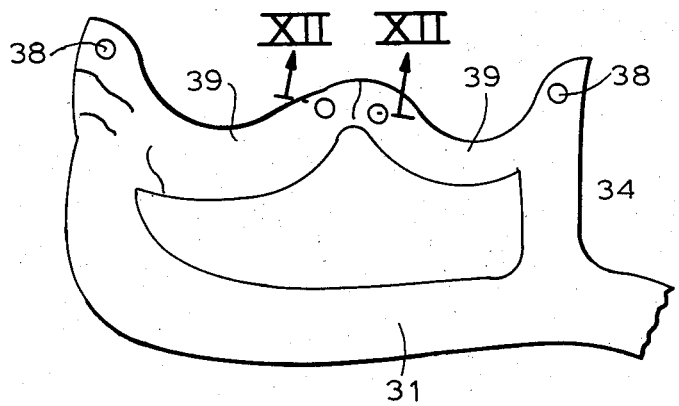
FIG. 15
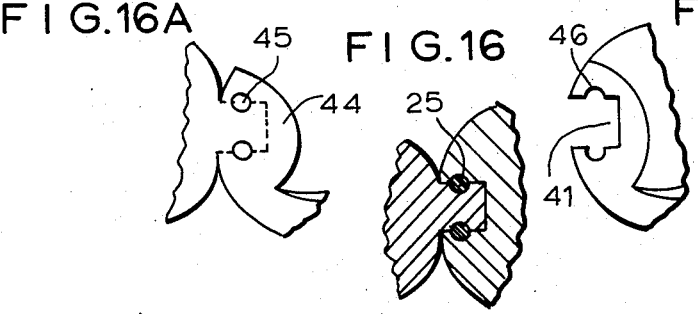
FIG. 16A   FIG. 16   FIG. 16B

METHOD OF MANUFACTURING DENTURES

BACKGROUND OF THE INVENTION

The present invention relates to methods of producing artificial teeth.

As known in dental practice, in producing dentures, an outer crown is mounted on a primary part, for example an inner crown which is rigidly installed in tooth stump, by means of a releasable holding element. Frequently, so-called locking bars or in other cases friction pins are employed as holding elements. In the case of the utilization of locking bars the secondary part is held on the primary part by a form-locking connection, and in the case of the use of friction pins the secondary part is mounted on the primary part by friction via force-locking connection. In both instances it is necessary that bearing recesses should be produced so as to receive the holding elements in a right position and with exact fit.

If a friction pin is employed as a holding element it is usually fixed on the secondary part and is inserted into a groove-shaped recess formed in the primary part; in this case sufficient friction between the walls of the recess and the pin should be ensured to prevent the possibility of lifting of the secondary part from the primary part.

If rotary locking bars are employed as holding elements those bars should be by rotation easily, but without play, inserted into the respective bearing recesses. It is particularly important in the case of rotary or pushing locking bars that the respective holes or recesses formed in the primary part and in the secondary part should be exactly alighed with each other. When friction pins are utilized it is important that these pins should be rigidly mounted in the holes or recesses formed in the secondary parts so that the alignment or orientation of these pins will be defined by those holes. It should be noted that the quality of denture techniques depends upon the precision of shapes and alignment of the holes or grooves for receiving holding elements connecting the parts of the denture to each other.

The manufacturing of artificial teeth in the conventional art is performed in the following manner:

First, an inner crown, which is later rigidly installed in a tooth stump, is produced in a usual fashion. After usual casting, finishing and polishing of the inner crown, the outer crown is modelled from wax. In the metal inner crown one forms a groove for a locking bar by a milling cutter, after removing the outer crown from the wax model. Then the wax model is again installed on the inner crown and the groove will be exposed by means of a knife for wax modelling. An auxiliary wire pin is then inserted into the groove as a temporary post for a further locking bar, which wire pin is covered with wax. The wax model is thereafter again lifted from the inner crown and casted with the wire pin embedded therein.

In known methods, grooves for receiving holding elements in the inner crown are also milled or drilled whereas the bearing surfaces for the holding elements in the secondary part may be formed during the casting of the outer crown. In such a process required allowances can not be warranted, and the bearing grooves and surfaces in both parts of the artificial tooth must be precisely aligned later on. This in many instances requires time-consuming finishing work; for example drilling of one or more holes is required in order to obtain a desired fit of the outer crown on the inner crown on the one hand, and, on the other hand, to obtain proper slidable insertion of the locking bar into the respective hole without the use of excessive force.

Similar methods are used in manufacturing of bridges or partial dentures when, for example, a secondary part is anchored to a bar connecting two crowns or to a supporting frame of one crown. Bearing holes are then drilled or milled in the bar of the primary supporting frame whereas the bearing holes in the secondary part are produced by means of an auxiliary post during the casting process. Corresponding processing steps are used in the producing of so-called groove-shoulder pin-guides for sedimentary material, which are advantageously made for removable artificial teeth to provide proper guidance for sedimentary material always occurring on the oral surface. Therefore, guiding grooves are milled in the primary parts, which grooves also serve for increasing friction force and for guiding the outer or secondary parts to be aligned on the primary parts. The corresponding grooves in the secondary parts are produced during the casting.

Conventional methods are utilized when noble metal alloys are employed as a working material for inner and outer crowns or primary and secondary parts. When non-noble metal alloys are employed such known methods can not be used because due to the great hardness of those alloys, for example in case of Cr-Ni-alloy, the drilling of holes in such materials by known methods is impossible. Due to the fact that in working with non-noble metal alloys substantially high temperatures are involved, grooves for receiving holding elements can not be produced by casting either, because usual auxiliary posts are not suitable for such temperatures. The customarily used soldering of the connecting elements in the parts of the denture with non-noble metal alloys is impossible since it causes subsequent absorption of the solder by ceramic facing material. Finally, it should be considered that in a casting process with non-noble metal alloys, the reaction between the flowing metal and an embedded mass takes place, which can cause the formation of a thin layer on the surface of the metal. The thickness of the layer depends upon a number of factors and can not be anticipated. Therefore, small deviations in the size of cast objects are unavoidable so that sufficient friction of two telescopically installed elements, with the outer part of the non-noble metal alloy, can not be warranted. In brief, it should be noted that good-quality artificial teeth from non-noble metal alloys could not be produced by conventional methods although it is has been desired to use such alloys in dental techniques since costs of noble metals constantly increase lately.

SUMMARY OF THE INVENTION

It is an object of the invention to provide an improved method of manufacturing artificial teeth.

Another object of the invention is to provide a method which is universal for use of noble-metal materials and non-noble metal alloys.

Still another object of the invention is to provide a method which substantially reduces costs and time involved in the production of artificial teeth and at the same time ensures a desired fit of the secondary part of the denture on the primary part thereof.

A further object of the invention is to ensure the proper fit between the recess for receiving the holding element and the holding element to be inserted therein.

These and other objects of the invention are attained by a method of manufacturing dentures, such as crown bridges, partial or complete dentures, including a preformed metal primary part and a preformed metal secondary part which is coupled to the primary part by at least one releasable holding element, the method comprising the steps of forming a recess for receiving a holding element in the primary part, forming a recess for receiving the holding element in the secondary part, at least one of said recesses through which the holding element is movably guided being produced by sparking erosion.

The one recess may be produced by sparking erosion in the primary part.

The recess in the primary part and the recess in the secondary part may be produced by sparking erosion The secondary part is totally preformed and in its final form is set on the primary part, the recesses being made in the primary and secondary parts thereafter in one working step by sparking erosion.

According to the invention a very precise fit is obtained in one part of the denture, in which part a holding element is movably guided so that in the case of the locking bar the latter may be slightly pivoted in the hole and in the case of the friction pin sufficient friction is ensured. Since the holding element is often non-releasably mounted in the secondary part it is suggested that the recess in the primary part will be in each case produced by sparking erosion. The fit in the primary part depends upon the orientation of the holding element which is rigidly mounted in the recess of the secondary part. It is also advantageous that the recess in the secondary part may be produced by sparking erosion. It is particularly advantageous that the recesses in the primary and secondary parts are made in one processing step by the same electrode so that both parts may be installed on the model in the proper position.

Electro-erosion method, which was not used before in dental techniques, has a number of significant advantages. First, cross-sections of the recesses which are produced by electroerosion methods according to the invention may be freely selected in accordance with the commercial needs and so as to be suitable for receiving holding elements of different sizes. By utilizing the same electrode of the cross-section corresponding to the cross-section of the recesses to be formed in the primary and secondary parts a precise guidance for the locking bar in both parts is warranted. Additional finishing of the recesses is not required. All inaccuracies in profiling of the secondary parts in the casting process have no effect on the fit of the holding elements within the recesses. Finally, the electrode can be so made that it can be applied fundamentally from the lingual side. In the sparking-erosion method no direct contact between the working piece and the electrode takes place whereas in producing holes by drilling or milling substantial pressure just be exerted whereby the deformations of thin side walls of the parts can not be excluded.

By utilizing the electro-erosion method throughholes, bores, or grooves for guiding locking bars or friction pins may be produced even in hard metal working materials without any difficulties. Parts of the artificial teeth produced by the method of the invention are reliably anchored to each other even when both parts are formed of non-noble metal alloys.

In contrast to known constructions in which at least the outer part is made out of noble metal alloy, the method of this invention substantially reduces production costs. It should be noted that the method of the invention is also applicable when the primary and secondary parts are formed of noble metal.

It is, of course, to be understood that the grooves or recesses may be formed in the primary and secondary parts in separate processing steps if this is required by orientation of the parts relative to the electro-erosion machine. However, it is particularly advantageous when the secondary part is turned over the primary part and the recesses are made in one step in the finally properly assembled parts. Thereby, perfect alignment of both recesses of the bearing into which the locking bar is later inserted, is ensured, without any additional working. Such an alignment is particularly important in the case of the use of friction pins since this alignment depends on the accuracy of the hole in the secondary part, which hole will not align with the groove in the primary part in the assembly if the preliminary alignment of the groove and the hole was not made.

According to further features of the invention the recess for receiving the friction pin may be formed by sparking erosion in a bar interconnecting two adjacent crowns.

Furthermore, the recess for receiving the friction pin may be formed by the sparking erosion in the transition zone provided between two adjacent crowns.

In the case when a pushing distributing bracket is used, the recess for receiving the friction pin may be formed by the sparking erosion in said bracket.

The recess in the primary part may be formed as a gutter-shaped groove and the recess in the secondary part may be formed as a gutter-shaped groove, said grooves being set in alignment to form together a recess for receiving a holding element. The holding element may be soldered within one of said recesses to connect the primary part to the secondary part.

In the case when a friction pin is used having two portions, one of said portions may be soldered within one of said recesses formed as a blind opening, and the other of said portions being bent to said one portion may be connected to the assigned part by acrylate.

The method of the invention may further include the step of forming guiding surfaces for sedimentary material in the primary part by sparking erosion.

These guiding surfaces may be made by forming a notch in the primary part and a complementary projection in the secondary part to form T-shaped surfaces, the recesses in the form of gutter-shaped grooves being produced in the primary and secondary parts, which grooves in assembly form a common recess for receiving a friction pin.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 is an exploded view in section, of the denture parts to be coupled with a locking bar;

FIG. 5 is a sectional view of the assembled denture of FIG. 4;

FIG. 6 is a top plan view of a washer shown in FIG. 5;

FIG. 6A is a side view of the pushing locking bar shown in FIG. 5;

FIG. 7 is a view of a primary part having two inner crowns interconnected with a bar;

FIG. 8 is a sectional view along line VIII—VIII of FIG. 7;

FIG. 9 is a sectional view through the secondary part shown in FIG. 8;

FIG. 10 is a sectional view of the secondary part with the locking bar of another embodiment;

FIG. 11 is a side view of the primary part including two adjacent crowns;

FIG. 12 is a view of the secondary part corresponding to the part of FIG. 11;

FIG. 13 is a section on line XIII—XIII of FIG. 11;

FIG. 14 is a section on line XIV—XIV of FIG. 12;

FIG. 15 is an exploded view of the primary and secondary parts to be coupled according to a further embodiment of the invention;

FIG. 16A is a partial view of the secondary part of FIG. 15;

FIG. 16 is a partial sectional view of two parts coupled with one another; and

FIG. 16B is a partial view of the primary part also shown in FIG. 16.

DETAILED DESCRIPTION OF THE PREFERRED EMBODIMENTS

Figure 1:
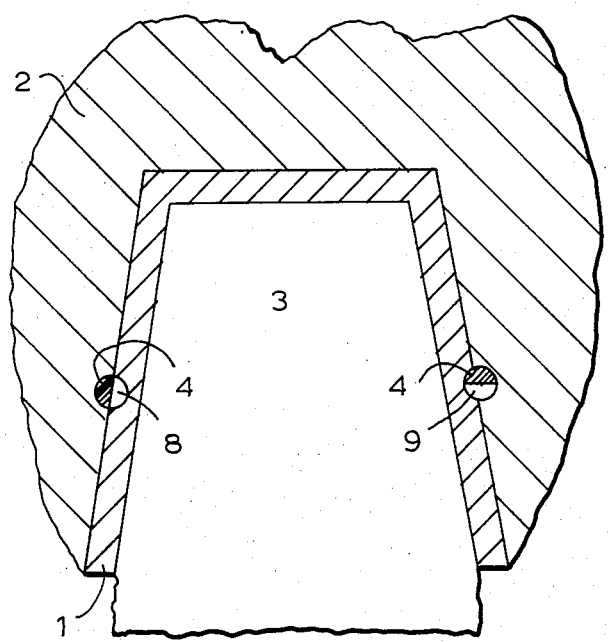
FIG. 1 is a partial sectional view through a primary part and a secondary part of the denture formed with recesses to receive a locking bar, produced by the method according to the invention.
Figure 3:
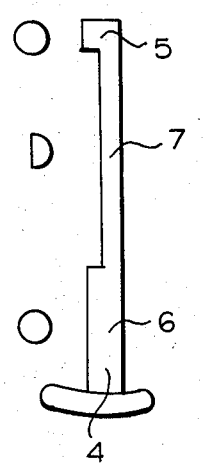
FIG. 3 is a side view of the locking bar.
Figure 2:
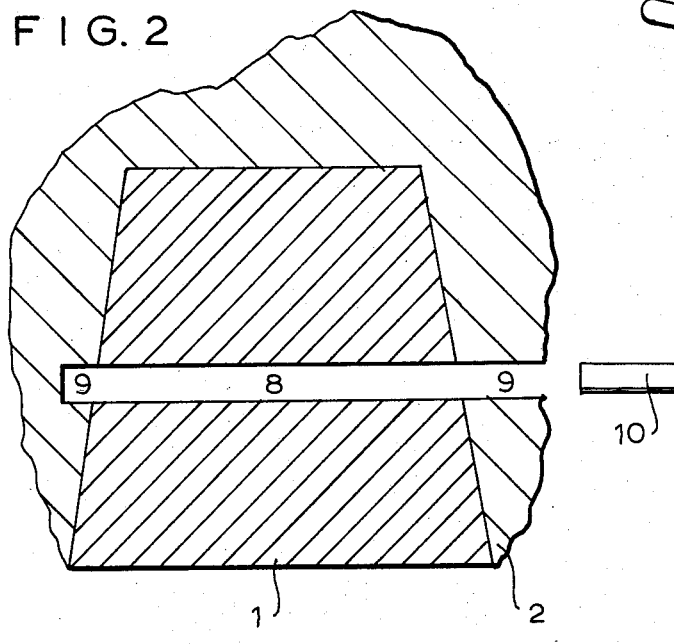
FIG. 2 is a partial sectional view along the recess shown in FIG. 1.

Referring now to the drawings, and first to FIGS. 1-3 thereof illustrating one of the embodiments of the present invention, it can be seen that reference character 1 denotes an inner crown which is a primary part of the denture whereas reference numeral 2 indicates an outer crown which is a secondary part of the denture. Numeral 3 designates a tooth stump of a denture model about which the inner crown 1 is formed. The inner and outer crowns are connected to each other by means of at least one rotary locking bar 4. FIG. 3 illustrates such a locking bar in detail. Locking bar 4 includes two portions 5 and 6 of circular cross-section and an intermediate portion 7 of semi-circular cross-section extended therebetween. Locking bar 4 tightly fits in a bearing-like recess 8 formed in the inner crown and recess 9 provided in the outer crown.

If locking bar 4 is received in the recesses 8 and 9 in the manner shown at the right side of FIG. 1 the outer crown is locked with the inner crown. If locking bar 4 is turned 90°, as shown at the left side of FIG. 1, outer crown 2 may be lifted from the inner crown 1.

FIGS. 1 through 3 show the first embodiment of the present invention, in which gutter-shaped grooves serve as bearing surfaces or recesses for receiving holding elements formed as rotary locking bars. These grooves 8 and 9 must very precisely align with one another; in practice they are actually formed as one circular bore into which rotary bar 4 is, without a play but rather easily, slidably inserted. Therefore, it is possible to form both grooves 8 and 9 in the primary and secondary parts without further refinishing, by means of one electrode 10 in one processing step by electro-erosion. It has been proved advantageous first to clamp the inner crown 1 mounted on its support, e.g. tooth stump 3 of the denture model, in the electroerosion or spark-erosion machine and to orient the face of the crown on the tooth stump 3 at the proper height such that an auxiliary electrode with a semicircular corss-section may be used, preferably for forming a recess as shown at the left side of FIG. 1. Without charging the position of the inner crown 1, the auxiliary electrode can be then replaced by the electrode 10 with the circular cross-section and the outer crown 2 can be adjusted to its final anatomically right position on the inner crown 1. A circular bore will be then formed by the electrode 10 in so-assembled unit, which electrode will penetrate the lingual wall of the outer crown and terminate at the opposite wall to form a blind hole. The recesses may be first made as blind holes and subsequently formed as gutter-shaped grooves.

Reference is now made to FIGS. 4 through 6 illustrating another embodiment of the invention, in which denture 11 is provided with a metal supporting frame 12. Denture 11 is coupled by a bar 13 extended between two primary crowns. FIG. 4 shows a strong bar 13 which may be a bar-like projection provided on one primary crown. This bar is made out of non-noble metal, preferably Ni-Cr alloy. Supporting frame 12 has a projection 14 integral therewith which penetrates the facing material of the denture and may be seen on the outer face thereof. Electrode 10, in this case, may be applied, without any additional means, directly to the metal part of the denture, particularly when the remaining parts of the denture are made of synthetic plastic material or ceramic facing material. If the supporting frame 12 (denture saddle) is turned about bar 13 a bore may be formed in the secondary part 12 and in the primary part 13 by electro-erosion in one processing step.

In the above described case both parts of the denture are locked by pushing locking bars. Such a pushing locking bar 15 has two cylindrical portions of different diameters. A slotted washer 16 having an opening corresponding to a thinner portion of bar 15 is clamped on the bar 15. This unit will be then inserted into a bore formed in the primary and secondary parts, and washer 16 will be glued to or embedded in the facing material of denture 11.

In the embodiments shown in FIGS. 1-3 and 4-6, the locking bar has been used as a holding element. Further figures illustrate the constructions with friction pins. As seen in FIG. 7 the primary part includes two crowns 20 and 21 which are connected to each other by bar 13. The primary part in FIG. 8 is mounted on the denture model and carries a properly positioned on and adjusted thereto secondary part of which denture saddle 22 is seen. Electrode 10 is applied to the unit to form bore 23 in the secondary part and bore 24 in the bar 13 of the primary part somewhat midway of the unit. A friction pin 25 is inserted into bore 23 and fixed in the secondary part 22. This step is preferably performed when both parts are still mounted on the denture model to thus ensure the proper alignment of pin 25. Then the secondary part is completely formed as shown in FIG. 9. FIG. 10 illustrates a modification of FIG. 9, in which pin 25 is formed with an upper bent projection 25'. In this modification the pin 25 may be soldered in the bore and/or fixed with its projection 25' to secondary part 22 by acrylate. FIG. 10 further illustrates the embodiment, in which a groove 26 is made in the lateral wall of the denture saddle 22. Accordingly, bar 13 is inserted into the lateral groove made by electro-erosion in the position offset from the center. The embodiment of FIG. 10 may be recommended when a thin-walled locking bar is required.

FIGS. 11-14 depict still another embodiment of the invention.

FIG. 11 shows a view of a primary part with two adjacent crowns whereas FIG. 12 illustrates partially shown secondary part to be coupled with the primary part. As seen in FIG. 13 two grooves 31 and 32 are formed in adjacent lateral walls of crown 30, which grooves extend into respective blind openings 33. The secondary part 34 (FIGS. 12 and 14) has in its supporting surface two holes 36 joined with gutter-shaped grooves 37. Pins 25 are inserted into holes 36 and soldered therein. Pins 25 are guided in grooves 37 over the most part of their length and extend downwardly over the supporting face material. Pins 25 in assembly are plugged in the blind openings 33 of the primary part. In the embodiment shown in FIGS. 11-14 recesses are formed also for receiving holding elements in the transition zone between two adjacent crowns. Additionally, recesses 38 can be formed at the ends of the pushing distributing bracket 39. Thus, in assembly the secondary part may be coupled with the primary part at four points.

FIGS. 15-16 illustrate a still further embodiment of the invention. In this embodiment in which electroerosion method can be also utilized, guiding surfaces for sedimentary material are provided. Crown 40 illustrated at the right side of FIG. 15 shows a recess or notch 41 of rectangular cross-section formed by an electrode in electroerosion process. Recess 41 is open towards the adjacent secondary part 42 shown at the left side of FIG. 15. If secondary part 42 is formed away from the primary part 40 a complementary projection 43 may be obtained on the part 42. Secondary part 42 will then set on the primary part 40 by inserting projection 43 into recess 41. As seen in FIG. 16A, in a supporting part 44 two through-holes 45 are formed which change over into corresponding grooves. In this process grooves 46 in the recess 41 are formed simultaneously with holes 45 by electroerosion. Pins 25, which are fixed on the secondary part 42 and extend partially into the grooves of the primary part and partially into the grooves of the secondary part, couple both parts together as shown in the sectional view of FIG. 16. In this manner a T-shaped guide for sedimentary material is provided. It is understood that a recess may be formed in the secondary part and a corresponding projection may be made on the primary part.

In the structures shown in the drawings circular bores or gutter-shaped grooves are formed. It is to be realized that holes or grooves of any other cross-sections may be, without any difficulties, used for coupling two parts of the denture, and any kind of holes or grooves may be produced by electroerosion method. For example, oval or conical holes may be suggested for receiving holding elements coupling the parts of the denture. It is also advantageous to provide vertically oriented locking bars instead of horizontally extended bars and horizontally projected pins in place of vertical friction pins. Of course, the method of the invention can be applied to other structures of holding elements, for example clamping constructions In the method of the invention the primary and secondary parts of the denture are completely preformed before holes and grooves for holding elements are made therein. Therefore, significant savings in time and costs of production can be obtained, as compared to conventional methods in which noble metals are used. These cost savings may be achieved because, due to utilization of electroerosion method, the secondary part formed of non-precious metal alloy can be anchored to the primary part also made out of non-precious metal.

It will be understood that each of the elements described above, or two or more together, may also find a useful application in other types of methods of producing dentures differing from the types described above.

While the invention has been illustrated and described as embodied in a method of manufacturing dentures, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of manufacuting dentures, such as crown bridges, partial or complete dentures and the like, including a preformed metal primary part and a preformed metal secondary part which is coupled to the primary part by at least one releasable holding element, the method comprising the steps of setting the secondary part totally preformed to its final form on the preformed primary part and forming in said primary part and said secondary part recesses simultaneously in one working step by sparking erosion, said recesses together constituting an opening for receiving said holding element, said holding element being soldered within one of said recesses to connect the primary part to the secondary part.

2. The method as defined in claim 1, in which a holding element used is a locking bar, said recesses in the primary and secondary parts being formed so that they extend in a horizontal direction.

3. The method as defined in claim 2, including the step of providing on the secondary part a projection outwardly extending from the remaining part of the secondary part through a facing material and integral with the secondary part, said projection facilitating the application of an electrode to said parts to produce said recesses.

4. The method as defined in claim 1, in which a holding element used is a friction pin, said recesses in the primary and secondary parts being formed so that they extend in a vertical direction.

5. The method as defined in claim 4, wherein the recess for receiving the friction pin is formed by sparking erosion in a bar interconnecting two adjacent crowns.

6. The method as defined in claim 4, wherein the recess for receiving the friction pin is formed by the sparking erosion in a transition zone provided between two adjacent crowns.

7. The method as defined in claim 4, in which a pushing distributing bracket is used, the recess for receiving the friction pin being formed by the sparking erosion in said bracket.

8. The method as defined in claim 4, wherein said recess is formed partially as a blind bore and partially as a gutter-shaped groove.

9. The method as defined in claim 4, wherein the recess in the primary part is formed as a gutter-shaped groove and the recess in the secondary part is formed as a gutter-shaped groove, said grooves being set in alignment to form together a recess for receiving a holding element.

10. The method as defined in claim 4, wherein a friction pin is used having two portions, one of said portions being soldered within one of said recesses formed as a blind opening, and the other of said portions being bent to said one portion and being connected to the assigned part be acrylate.

11. The method as defined in claim 4, including the step of forming guiding surfaces for sedimentary material in the primary part by sparking erosion.

12. The method as defined in claim 4, wherein said guiding surfaces are made by forming a notch in the primary part and a complementary projection in the secondary part to form T-shaped surfaces the recesses in the form of gutter-shaped grooves being produced in the primary and secondary parts, said grooves in assembly forming a common recess for receiving a friction pin.

13. The method as defined in claim 1, wherein the primary and secondary parts are made out of noble metal.

14. The method as defined in claim 1, wherein the primary and secondary parts are made out of non-noble alloy.

* * * * *